United States Patent [19]

Charlie et al.

[11] Patent Number: 5,109,702
[45] Date of Patent: May 5, 1992

[54] METHOD FOR DETERMINING LIQUEFACTION POTENTIAL OF COHESIONLESS SOILS

[75] Inventors: Wayne A. Charlie, Fort Collins, Colo.; Leo W. Butler, Green Bay, Wis.

[73] Assignee: The United States of America as represented by the Secretary of the Air Force, Washington, D.C.

[21] Appl. No.: 549,888

[22] Filed: Jun. 27, 1990

[51] Int. Cl.$^5$ ............................................. G01N 3/00
[52] U.S. Cl. ............................................................ 73/84
[58] Field of Search ..................................... 73/784, 84

[56] References Cited

U.S. PATENT DOCUMENTS

| | | | |
|---|---|---|---|
| 3,456,509 | 7/1969 | Thordarson | 73/406 |
| 3,561,259 | 2/1971 | Barendse | 73/84 |
| 3,906,781 | 9/1975 | Vlasblom | 73/784 |
| 4,408,481 | 10/1983 | Sidey | 73/73 |
| 4,411,160 | 10/1983 | Lutenegger et al. | 73/843 |
| 4,453,401 | 6/1984 | Sidey | 73/73 |
| 4,594,899 | 6/1986 | Henke et al. | 73/784 |
| 4,649,741 | 3/1987 | Strom | 73/84 |

FOREIGN PATENT DOCUMENTS 1214840 2/1986 U.S.S.R. ................................. 73/84

Primary Examiner—Robert Raevis
Attorney, Agent, or Firm—Thomas C. Stover; Donald J. Singer

[57] ABSTRACT

A method for determining the liquefaction potential of cohesionless (granular) soils is provided in which a rotational shear vane assembly having a plurality of radially disposed blades (herein a Piezovane) is mounted to a shaft having a porewater pressure transducer mounted to such assembly and communicating to an outer edge of at least one the blades, with a torque transducer mounted to such shaft and a potentiometer connected to an upper portion of the shaft to measure rotational displacement of such blades. The vane assembly blades are inserted into undisturbed soil and rotated one or more turns to obtain porewater pressure response measurements from the soil shear surface defined by the blade ends along with torque and rotational displacement measurements. A porewater pressure increase indicates a contractive soil which has the potential to liquefy (and cause landslides) while a porewater pressure decrease indicates a dilating soil which does not readily liquefy and is suitable for building thereon.

18 Claims, 4 Drawing Sheets

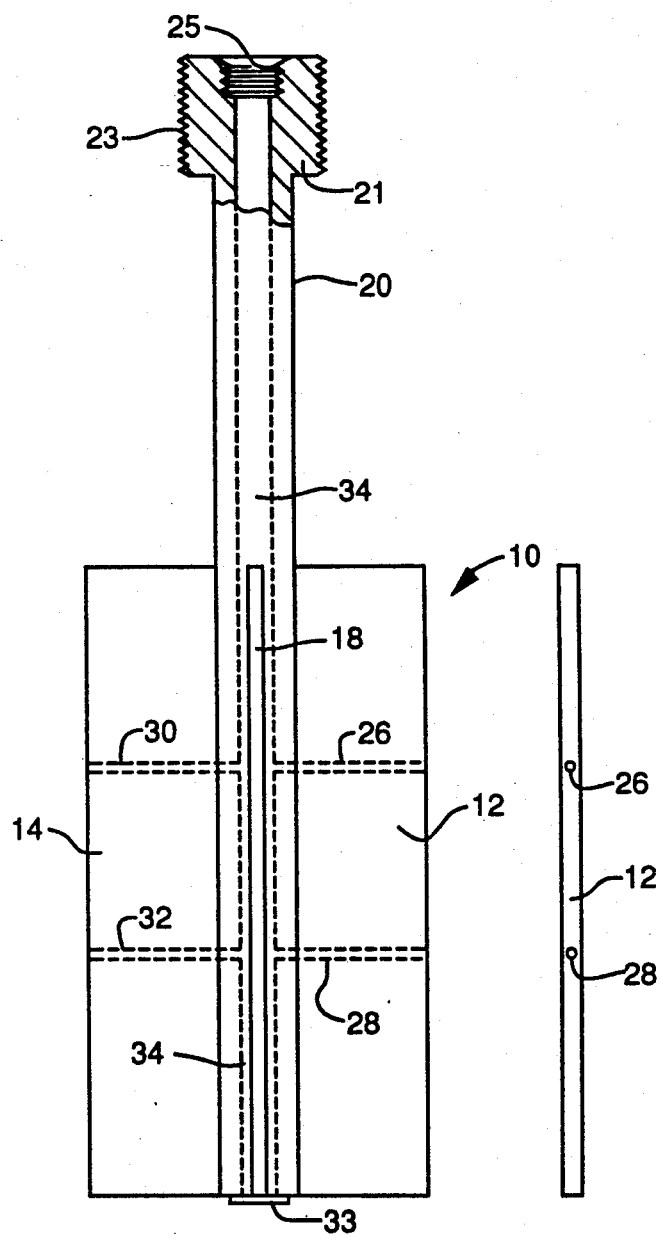
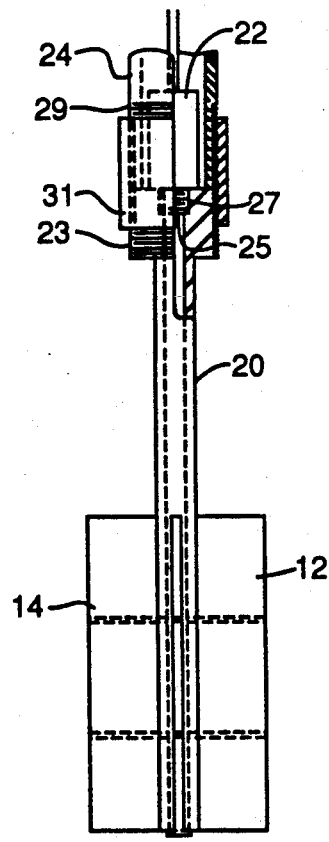
FIG. 1
FIG. 2
FIG. 4
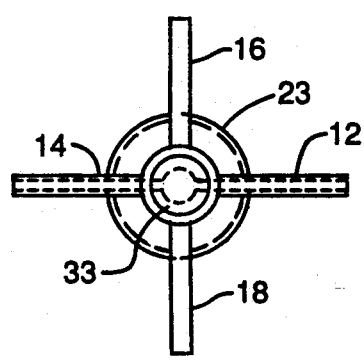
FIG. 3

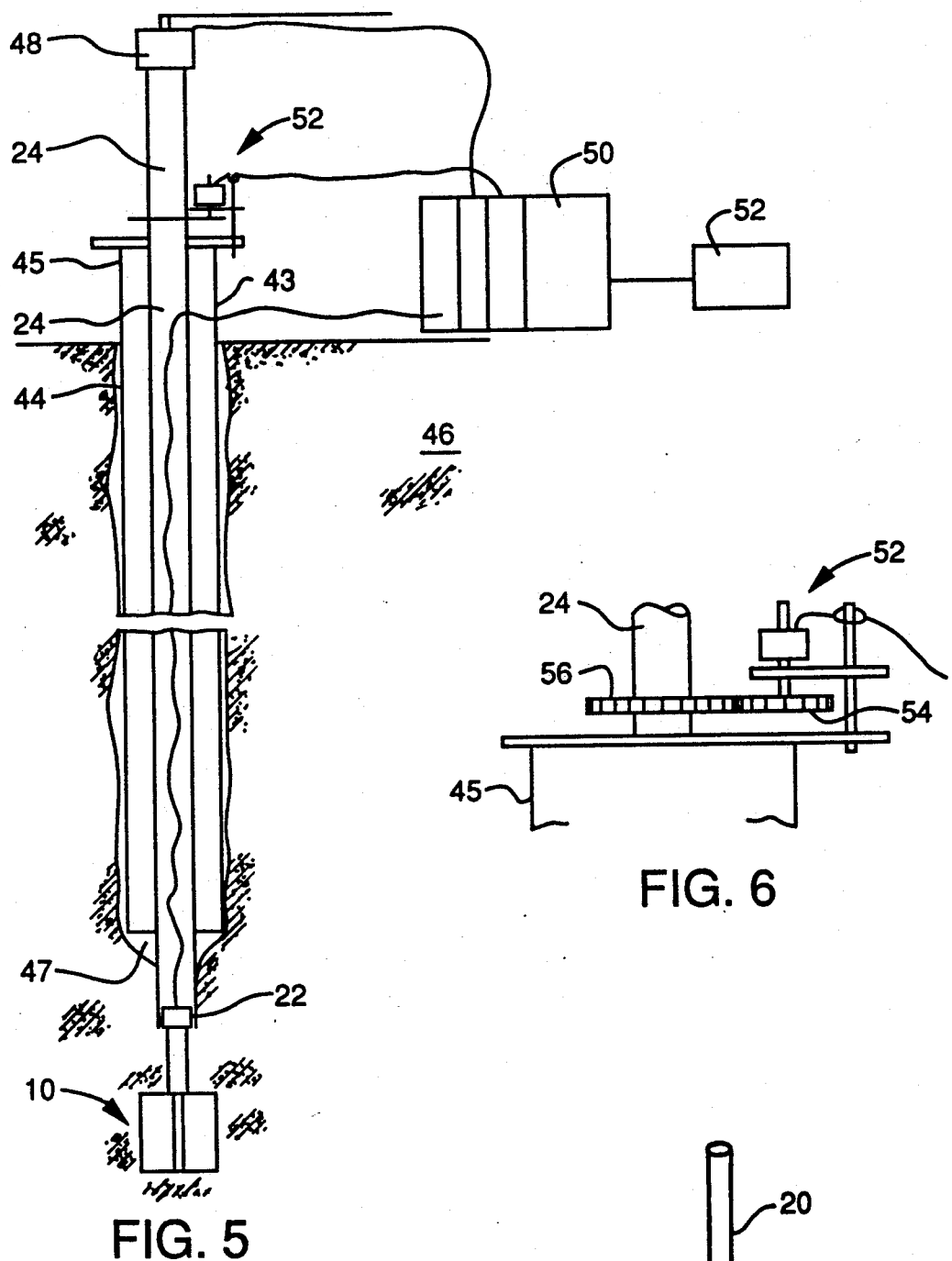
FIG. 5
FIG. 6
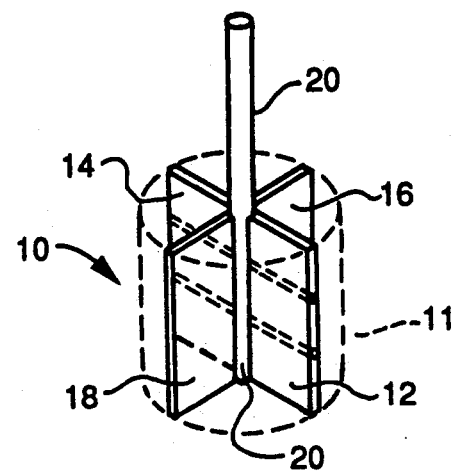
FIG. 11

METHOD FOR DETERMINING LIQUEFACTION POTENTIAL OF COHESIONLESS SOILS

STATEMENT OF GOVERNMENT INTEREST

The invention described herein may be manufactured and used by or for the Government for governmental purposes without the payment of any royalty thereon.

BACKGROUND OF THE INVENTION

1. Field of the Invention

This invention relates to a method for determining liquefaction potential of soils, particularly a method for determining liquefaction potential, in-situ of cohesionless soils.

2. Description of the Prior Art

Soil liquefaction results from increases in soil porewater pressure induced by transient or repeated ground motions. Porewater pressure increases may be induced by earthquakes, explosions, impacts and ocean waves. Soil liquefaction occurs in water-saturated, cohesionless soils and causes a loss of soil strength that may result in the settlement of buildings, landslides, the failure of earth dams and pipelines, or other hazards. Liquefaction of sands and silts has been reported in almost all large earthquakes around the world. For example, an earthquake in 1964 caused more than one billion dollars in damages in Niigata, Japan. The Great Alaskan Earthquake in 1964 destroyed large sections of Valdez and Anchorage, and failed more than 250 bridges. The San Fernando, Calif., earthquake of 1971 resulted in the liquefaction induced failure of the Lower Van Norman Dam. Most of the damage that occurred during these earthquakes was due to widespread soil liquefaction.

For existing and planned structures, e.g., large mine tailing impoundments, earth fill dams, nuclear power plants and offshore structures, the liquefaction tendencies of a site should be studied so that preventative steps can be taken where possible.

Prior methods for evaluating liquefaction potential follow two basic approaches, laboratory tests and in-situ test procedures. The laboratory approach requires undisturbed samples. At the present time, there is not a method for obtaining undisturbed samples which does not alter the in-situ void ratio, structure, or stress state during removal. There are also questions on which laboratory test is more representative of actual field conditions. As for the other approach, four in-situ tests are being used to determine liquefaction potential. These are (1) the Standard Penetration Test (SPT), (2) the Cone Penetration Test (CPT), (3) The Piezocone Penetration Test (PCPT) and (4) Seismic Wave Tests (SWT).

The Standard Penetration Test (SPT) approach is based on an empirical correlation between the number of blows and the occurrence or nonoccurrence of liquefaction at sites subjected to past earthquakes. The SPT data is sensitive to technique and can vary by more than 50% among reputable drillers. The Cone Penetration Test (CPT) has several advantages over the SPT, but like the SPT test, empirical correlations between penetration resistance and liquefaction potential are used. The piezocone penetration test (PCPT) uses the CPT with a porewater transducer located on or behind the cone. There is some disagreement on the location of the pressure transducer and what is measured. A major disadvantage is that the soil displacement caused by the penetration of the cone and vertical stress increases caused by the advancement of the cone, influences the porewater pressure response. Seismic Wave Tests (SWT) are based on an empirical correlation between the velocity of shear waves and the occurrence or nonoccurence of liquefaction.

Samples of the above penetration tests are disclosed in e.g., in U.S. Pat. No. 4,453,401 to Sidey (1984) and U.S. Pat. No. 4,594,899 to Henkel et al. (1976), which disclosures are subject to the drawbacks noted above, relative to the SPT approach and CPT approach.

There have also been attempts to measure soil liquefaction potential by employing a shear vane test. In this approach a vane assembly, having a plurality of angularly spaced blades, is mounted to a drilling shaft, with torque sensors mounted either on the blades or the drilling shaft. The so-mounted vane assembly is lowered on the drilling shaft, into soil, rotated and torque measurements taken. Subsequently, mathematical calculations based on the respective torque measurements, result in an approximation of soil shear strength.

In another example of the prior art, a laboratory vane apparatus has been constructed wherein 4 blades at right angles are mounted on a rotational shaft with an aperture cut through one of the vanes which communicates with the interior of said shaft and to the upper portion thereof and thence to a hypodermic needle, for registering changes in pore pressure at the edge of such vane. The vane apparatus was lowered into a container of cohesionless soil such as silt or sand. The vane blades were rotated in the sand to shear same and describe a cylinder having the same dimensions as the (outer edges of the) vane blades. The blades were rotated slowly and porewater pressure fluctuations noted on the calibrations of the hypodermic needle. A number of tests were accordingly run in dense sand (dilative condition) and loose sand (contractive condition) and the porewater pressure noted. It was found that in the dense sand one would obtain negative porewater pressure readings and that in loose sand, one would obtain positive porewater pressure readings. The conclusion of such studies was that torque readings were distorted in cohesionless soils so as to indicate, in dense sand, an inflated stress reading while in loose sand, a deflated or reduced stress reading relative to shear strength was indicated. That is, the study concluded that one could not use rotating vane shear tests to obtain accurate shear strength calculations in cohesionless soil but only in cohesive soil such as clay. The study thus recommends against the use of a rotational vane apparatus for making shear strength related measurements in a cohesionless soil, see Wilson, N. E., 1963 "Laboratory Vane Shear Tests and The Influence of Pore-Water Stresses," *ASTM, Special Technical Publication*, No. 361, pp 377–388. For a related article see ASTM D 2573, 1972, re-approved 1978, "Standard Test Method for Field Vane Shear in Cohesive Soil," 1987, Annual Book of ASTM Standards, Vol 04.08, Phila, Pa., pp. 424–427.

Such article covers the field vane test in soft saturated cohesive soils with guide lines for conducting the test and also a formula for calculating shear strength of the soil from the torque applied to the vane apparatus.

Indications are from the above two articles, particularly the former, that one would not use a vane assembly for tests in cohesionless soils.

There has thus been no satisfactory test for measuring shear strength and liquefaction potential for water-saturated, cohesionless soil deposits. And there is a need and market for a procedure for such soil testing in which such soil is not locally compressed or otherwise deformed so as to introduce significant error into such measurements, which are important for e.g., site and foundation response studies.

There has now been discovered a method for obtaining the above needed data accurately, to determine therefrom the liquefaction potential and shear strength of cohesionless soils.

SUMMARY OF THE INVENTION

Broadly the invention provides a method for determining liquefaction potential of cohesionless soils comprising, employing a rotational vane assembly having a plurality of radially disposed blades mounted to a shaft and a pore pressure sensor mounted to such assembly and communicating to an outer edge of at least one blade. The blades are inserted into the soils and are rotated to shear the soils and obtain porewater pressure response measurements from the soil shear surface defined by the blade ends.

By "cohesionless soils" as used herein, is meant soils that do not normally cohere nor adhere together, such as silt, sand, gravel and the like.

BRIEF DESCRIPTION OF THE DRAWINGS

The invention will become more apparent from the following details specifications and drawings in which;

FIG. 1 is a fragmentary elevation view, partly in section of a portion of the vane assembly embodying the invention;

FIG. 2 is an end elevation of a component of the vane assembly of FIG. 1;

FIG. 3 is a bottom plan view of a vane assembly component embodying the invention shown in FIG. 1;

FIG. 4 is a fragmentary elevation view, partly in section, of additional components of the vane assembly embodying the present invention;

FIG. 5 is a partial sectional elevation view, partly in schematic, of the vane assembly embodying the present invention in operation;

FIG. 6 is a fragmentary elevation schematic view of a component of the vane assembly of the invention shown in FIG. 5;

FIGS. 9 and 10 graphs are test results using the vane assembly of the invention in dilating soils and FIG. 11 is a fragmentary perspective view of a component of the invention shown in FIG. 5.

DESCRIPTION OF THE PREFERRED EMBODIMENT

Figure 7:
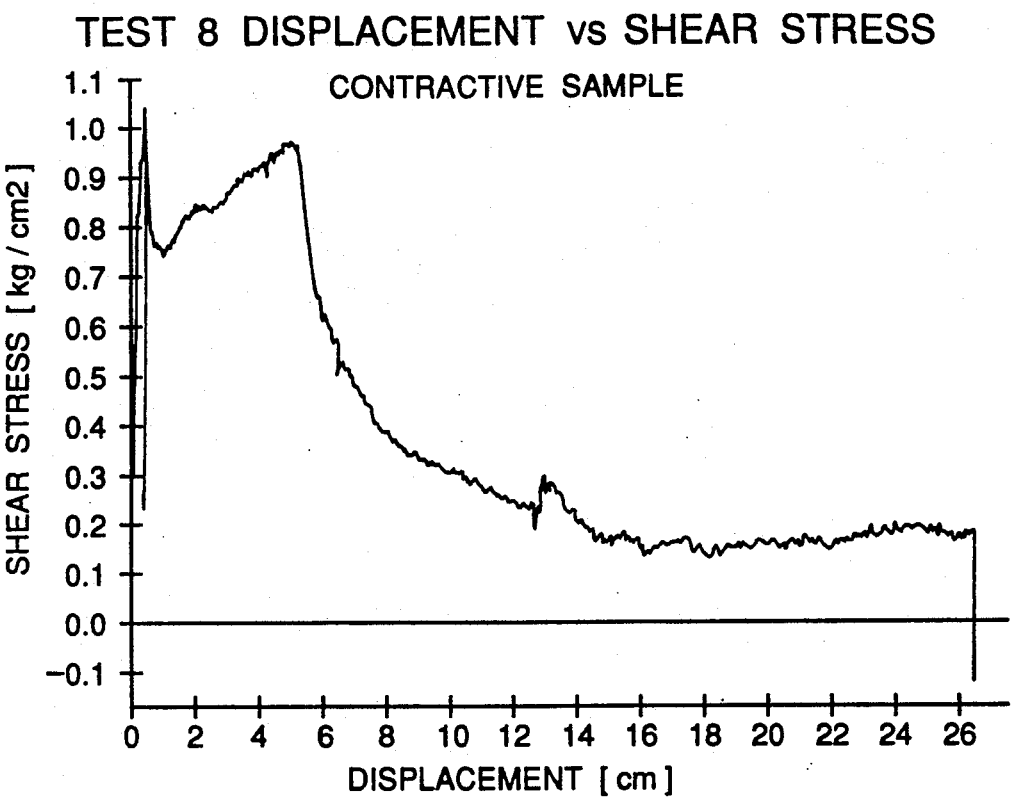
FIGS. 7 and 8 are graphs of test results employing the vane assembly of the invention in contractive soils.

Referring now to the invention in more detail, shear vane assembly 10 has blades 12, 14, 16 and 18, axially mounted to vane rod 20, which terminates in hollow nob 21, having exterior pipe threads 23 thereon and interior threads 25, as shown or indicted in FIGS. 1, 2, 3 and 4.

The porewater pressure transducer 22 has threaded extension 27 which screws into the threaded receptacle 25, of the vane rod 20, and thus is mountable within the hollow rotational rod 24, as shown in FIG. 4.

The hollow rotational rod 24 has exterior threads 29 which match the threads 23 so that the vane rod 20 and the rotational rod 24 can be joined by internally threaded couple 31, as shown in FIG. 4.

In operation, a test shaft 44 is drilled in a soil deposit 46 by a drilling rig (not shown). The drill being withdrawn, the shear vane assembly 10, mounted in hollow casing 43, is lowered into the shaft 44, with the upper portion of the casing 45 remaining above ground, as shown or indicated in FIG. 5. Atop casing 45 is a potentiometer 52, having gear 54 which engages gear 56, mounted around the hollow rotational rod 24, as shown or indicated in FIG. 6. The potentiometer 52 serves to measure the angle of displacement or percentage rotation of the shear vane assembly 10 below.

Further up on the rotational rod 24 is torque transducer 48, to measure the torque applied in rotating such vane assembly 10 in the water saturated soil below, as shown or indicated in FIG. 5.

Thus the vane assembly (or piezovane 10) of the invention includes a porewater pressure transducer, a torque transducer and a potentiometer. The porewater pressure transducer measures porewater pressure changes along the shearing surface. The torque transducer measures the torque required to shear the sample. Torque is a function of shear strength. The potentiometer measures the amount of displacement which has taken place during shearing. These instruments are continuously monitored by a data acquisition system 50, which is controlled by a computer as shown in FIG. 5. Data can be stored on disks for later analysis. The piezovane of the invention serves as an in-situ apparatus and method to determine 1) dilating and contractive states of cohesionless soils and 2) the steady-state shear strength thereof.

In further operation, the vane assembly 10 within the casing 45, is lowered to the bottom of the pre-drilled hole 44, where it contacts the undisturbed soil bottom 47, as indicated in FIG. 5. Thereafter the rotational rod 24 and vane assembly 10, are pushed downwardly (by means not shown) below the casing 45 and well into the water-saturated cohesionless soil (e.g., 4 to 5 lengths once into water saturated sand), as shown or indicated in FIG. 5.

The vane assembly 10 can also be pushed from the ground surface to the desired depth, without predrilling a hole in the soil, per the method of the invention.

Then the vane rotational rod 20 is rotated by rotational rod 24 (by means not shown) rapidly for at least one full turn, to induce a cylindrical failure shear surface 11 in the soil surrounding the vane blades, as indicated in FIG. 11. As the soil is failed, the torque, angular displacement and porewater pressure are recorded through one or more turns on the data acquisition system 50, which includes computer 52, as shown in FIG. 5

Following such tests, the shear vane assembly 10 is lowered to another depth in the undisturbed soil and the above testing procedure repeated. Such procedure is further repeated at increasing depth and at other locations to test the soils' liquefaction potential and its shear resistance, as discussed further below.

The shear vane assembly used in the method of the invention measures (preferably in previously undisturbed soil) the soils porewater pressure response on the induced failure surface, i.e., the sheared surface of the annular body described by the edges of the vane blades, eg., per FIG. 11. The vane is rapidly rotated and data recorded for the first rotation, so as to gather data for freshly sheared soil when it counts i.e., before the data values drop off. For example, after the first rotation, the porewater pressure is reduced as the water drains from the sheared surfaces.

The shear vane assembly employed in the method of the present invention was made to meet the ASTM D 2573 standard for the field shear vane test in cohesive soils. Such ASTM reference is cited above. In such standard there are 4 fins perpendicular to each other. For the method of the present invention, two pressure taps were added on to two opposing blades as described above with respect to FIG. 1. As shown in FIG. 1, the pressure taps or ducts 26, 28, 30 and 32 lead to passage 34 and thence to a pressure transducer 22 mounted atop the vane assembly 10, as discussed above. Such pressure taps allow the porewater pressure response at the soils (shear) failure surface, on the outside edge of the vanes, to be measured. It is however necessary that the cap 33 at the bottom of the vane apparatus, securely seal the duct passageway system, e.g., as shown in FIG. 1 so that such system is filled with water and free of air bubbles to give accurate readings on the pressure transducer 22. Readings of porewater pressure response to shearing of the previously undisturbed soil and of the vanes' torque and annular displacement, are recorded simultaneously by data recorders as noted above.

Thus the shear vane assembly or piezovane used in the method of the invention, is employed in-situ, to determine the liquefaction potential of water-saturated, cohesionless soil deposits. This is done by measuring the porewater pressure response during and after shearing the soil with such vane. That is, data is taken during the first complete rotation of the vane blades and for several minutes thereafter. In general, a porewater pressure increase (from such first rotation), indicates a soil which has the potential to liquefy while a porewater pressure decrease indicates a soil which tends not to or cannot liquefy.

In a preferred embodiment of the invention, a porewater pressure transducer is mounted in each blade at or near the outer edge thereof, with a torque transducer mounted on the vane shaft just above the vane blades.

As noted above, the shear vane assembly employed in the method of the present invention, measures the soils porewater pressure response on the induced failure surface, an annular body defined by the outer vane blade edges. This response during shearing as noted above, is an indication of the soils susceptability or resistance to liquefaction. That is, a positive porewater pressure response by a soil deposit under shear, indicates contractive behavior. When a contractive deposit is subject to large shear strains, the undrained steady state strength will be less than the initial drained strength. Therefore the soil deposit has a potential to liquefy if the appropriate triggering mechanism occurs. On the other hand, if the porewater pressure response is negative, then the deposit has dilative behavior. A dilative deposit is not susceptible to liquefaction since its undrained strength is greater than its drained strength.

For a saturated sand deposit to have a liquefaction failure, three conditions must exist:

(1) The undrained state steady strength of the sand deposit must be less than the initial drained strength, (2) The driving shear stresses must be greater than the undrained steady state strength and (3) a triggering mechanism must occur so that the drained condition is converted to an essentially undrained condition.

At the relatively fast rotation rates employed in the method of the present invention, the shear vane assembly disclosed herein is able to measure the undrained steady state strength and changes in porewater pressure. The shape of stress-strain curves shown below are also indicative of contractive or dilative behavior.

Thus as indicated above, the present invention provides a method for determining liquefaction potential of cohesionless soil deposits by measuring porewater pressure response at a shear surface of previously undisturbed soil.

To illustrate the use of the method of the invention in obtaining liquefaction data of cohesionless (granular) soils, the following Example is given and should not be construed in limitation thereof.

EXAMPLE I

A shear vane having four blades mounted at right angles similar to that shown in FIG. 1 with a vane diameter of 2½ in., a blade height of 5 in. and a blade thickness of 3/16 in. (with pressure tap passages 1/16" in diameter) having a porewater pressure transducer, torque transducer, potentiometer and data acquisition system connected thereto in the manner discussed above in respect e.g., with respect to FIGS. 1, 2, and 5, was lowered 3 ft. into undisturbed soil, in a water saturated contractive sand deposit and rotated at ¼ RPS (revolutions per second) for 1 full turn and readings of porewater pressure, shear strength and vane displacement were taken, from which the graphs of FIGS. 7 and 8 hereof were plotted.

The shear vane was then lowered into a pre-drilled hole in a water saturated, dilating sand deposit, the vane blades being pushed into and below the bottom of such hole by e.g., 5 ft. into undisturbed soil. The shear vane was then rotated at ¼ RPS for one turn and the above readings again taken, from which the graphs of FIGS. 9 and 10 were plotted.

Figure 8:
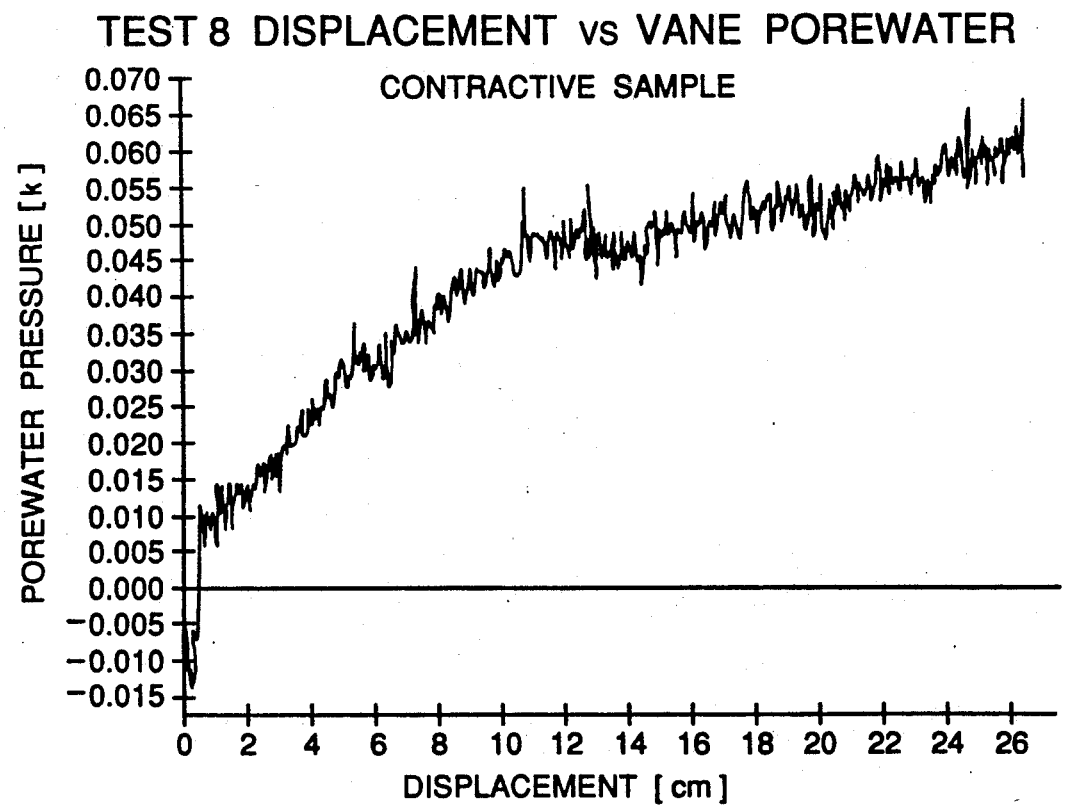

In contractive sands, the steady state shear strength is less than the peak shear strength, as shown in FIG. 7, while the porewater pressure increases with increasing vane displacement (for one full turn), as shown in FIG. 8.

Figure 9:
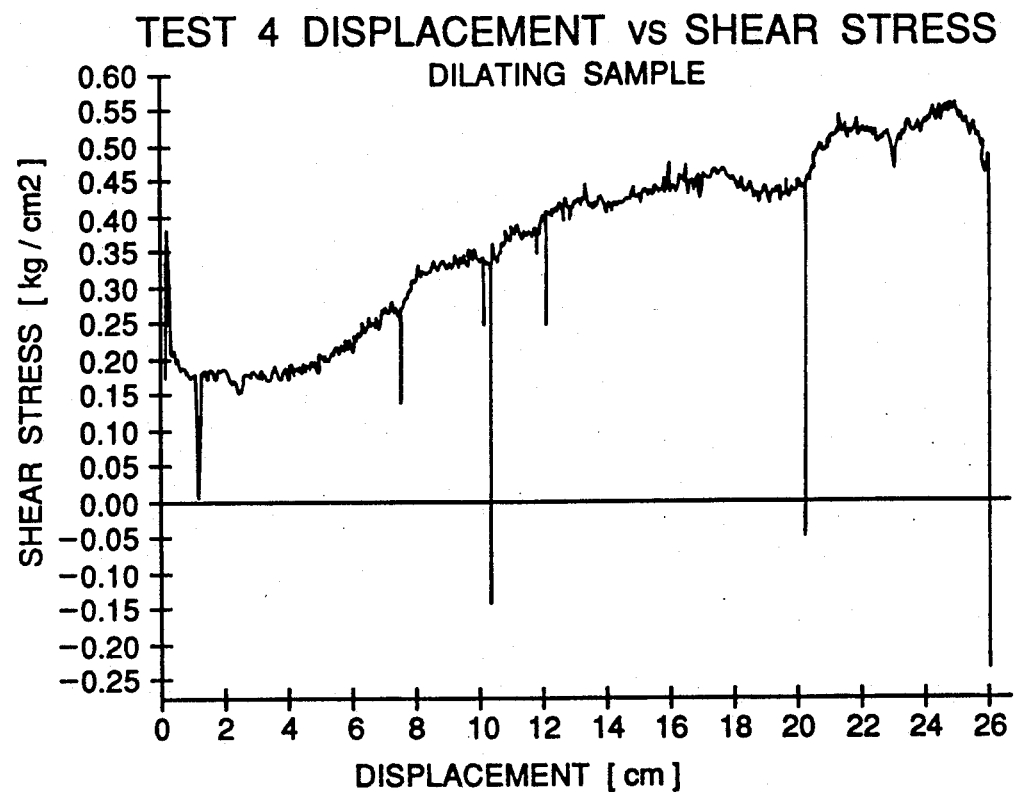
Figure 10:
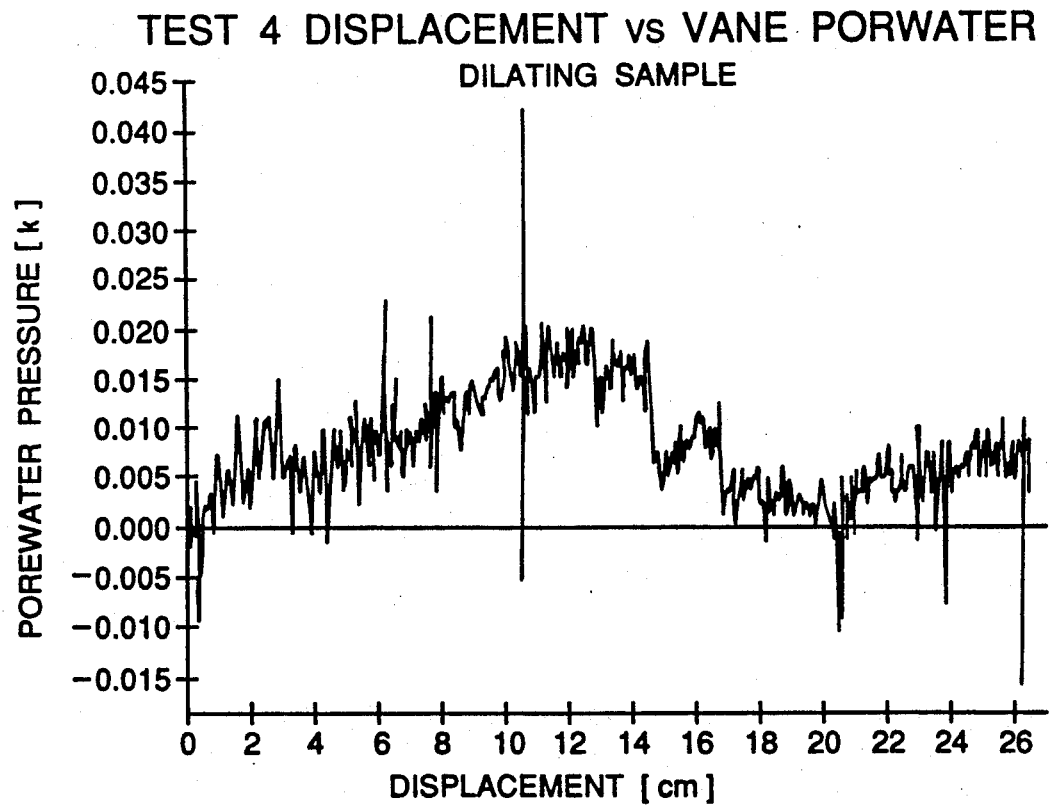

In dilating sands, the shear strength increases with increasing vane displacement for (one full turn) per FIG. 9, while the porewater pressure remains relatively unchanged, as shown in FIG. 10.

Thus the shear vane assembly or Piezovane of the invention is rotated in cohesionless (granular) soils to measure porewater pressure changes along the shearing surface and the torque required to shear a soil sample so as to determine 1) whether a solid is dilating or contractive and 2) the steady state shear strength. The thus measured porewater pressure response induced by shearing of such soil, is the basic parameter required for determining in-situ liquefaction potential of water saturated, cohesionless, soil deposits. A porewater pressure increase, indicates a soil which has the potential to liquefy (and cause landslides) while a porewater pressure decrease indicates a soil which does not liquefy and so is suitable for building structures thereon.

What is claimed is:

1. A method for determining liquefaction potential of cohesionless soils comprising, employing a rotational vane assembly having a plurality of radially disposed blades mounted to a shaft, a pore pressure sensor mounted to said assembly and communicating by a duct to an outer edge of at least one blade; inserting said blades into said soils; rotating said shaft to revolve said blades to shear said soils and obtaining porewater pressure response measurements from said soils.

2. The method of claim 1, wherein said measurements are obtained from the shear surface defined by the blade edges.

3. The method of claim 1 wherein said sensor is a pressure transducer mounted to said shaft and communicates by an duct through said shaft and at least one blade to the outer edge of the latter.

4. The method of claim 3 having a plurality of said apertures in each of two of said blades.

5. The method of claim 1 wherein said vane assembly has four blades radially mounted to said shaft.

6. The method of claim 1 wherein said cohesionless soils are selected from the group consisting of silt, sand and gravel.

7. The method of claim 1 wherein said blades rotate at from between ¼ to 10 RPS.

8. The method of claim 1 wherein said rotational vane assembly mounts on a drill rig for in-situ testing of said soils.

9. The method of claim 1 wherein said pore pressure sensor obtains data measurements for porewater pressure response to shearing, and other sensors measure the vane assembly's torque and angular displacement.

10. The method of claim 9 wherein a hole is drilled into the soil to be tested, the vane assembly is lowered into the hole and inserted into the soil at the base of said hole and then rotated to obtain the measurements of porewater pressure response, torque and angular displacement.

11. The method of claim 9 wherein, after said measurements are obtained, the vane assembly is pushed deeper into undisturbed soil, the vane assembly is rotated and data gathered as before and the above steps are repeated.

12. A rotational vane assembly for determining liquefaction potential of cohesionless soils comprising:
a rotatable shaft,
a plurality of radially disposed blades mounted to said shaft,
a pore pressure sensor mounted to said assembly and communicating by a duct to an outer edge of at least one blade,
means for inserting said blades into said soils and means for rotating said shaft to revolve said blades to shear said soils and obtain porewater pressure response measurements from said soils.

13. The assembly of claim 12 wherein said sensor is a pressure transducer mounted to said shaft and communicates by a passage through said shaft and through at least one blade to the outer edge thereof.

14. The assembly of claim 13 having a plurality of said passages in each of two of said blades.

15. The assembly of claim 12 wherein said vane assembly has 4 blades radially mounted to said shaft.

16. The assembly of claim 12 having means to rotate said shaft and blades at from between ¼ to 10 RPS.

17. The assembly of claim 12 being mountable on a drill rig for in-situ testing of said soils.

18. The assembly of claim 12 having additional sensors for measuring the assembly's rotational torque and angular displacement.

* * * * *